United States Patent
Arnold

(10) Patent No.: US 10,995,355 B2
(45) Date of Patent: *May 4, 2021

(54) METHODS FOR AMPLIFICATION OF NUCLEIC ACIDS UTILIZING CLAMP OLIGONUCLEOTIDES

(71) Applicant: Lyle J. Arnold, Poway, CA (US)

(72) Inventor: Lyle J. Arnold, Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/231,857

(22) Filed: Dec. 24, 2018

(65) Prior Publication Data

US 2019/0177760 A1   Jun. 13, 2019

Related U.S. Application Data

(62) Division of application No. 14/773,365, filed as application No. PCT/US2014/029850 on Mar. 14, 2014, now Pat. No. 10,202,629.

(60) Provisional application No. 61/789,585, filed on Mar. 15, 2013.

(51) Int. Cl.
| | |
|---|---|
| *C12Q 1/68* | (2018.01) |
| *C12P 19/34* | (2006.01) |
| *G05D 27/02* | (2006.01) |
| *H05B 47/175* | (2020.01) |
| *C12Q 1/6844* | (2018.01) |

(52) U.S. Cl.
CPC ............ *C12P 19/34* (2013.01); *C12Q 1/6844* (2013.01); *G05D 27/02* (2013.01); *H05B 47/175* (2020.01)

(58) Field of Classification Search
CPC ............ C12Q 1/6844; C12Q 2525/307; C12Q 2533/107; C12Q 2565/50; C12P 19/34
See application file for complete search history.

(56) References Cited

U.S. PATENT DOCUMENTS

| | | | | |
|---|---|---|---|---|
| 10,202,629 | B2 * | 2/2019 | Arnold | C12P 19/34 |
| 2004/0137484 | A1 * | 7/2004 | Zhang | C12Q 1/682 |
| | | | | 435/6.11 |
| 2006/0234264 | A1 * | 10/2006 | Hardenbol | C12P 19/34 |
| | | | | 435/6.12 |

* cited by examiner

*Primary Examiner* — David C Thomas

(57) ABSTRACT

The present invention provides methods of amplifying a target nucleic acid utilizing a clamp oligonucleotide comprising a first target-binding region on the 3'-terminus and a second target-binding region on the 5'-terminus and tether region in between. The tether region may comprise a variety of user-defined sequences or elements that allow for further manipulation of the target nucleic acid. Such as, for example, capture followed by amplification, identification and/or sequencing. The target-binding regions bind to the target nucleic acid, the 3'-terminus functions as a primer to initiate extension across the target nucleic acid sequence and ligation of the gap results in formation of a circularized nucleic acid. This circular template can be used in a variety of processes, including amplification and sequencing.

1 Claim, 1 Drawing Sheet

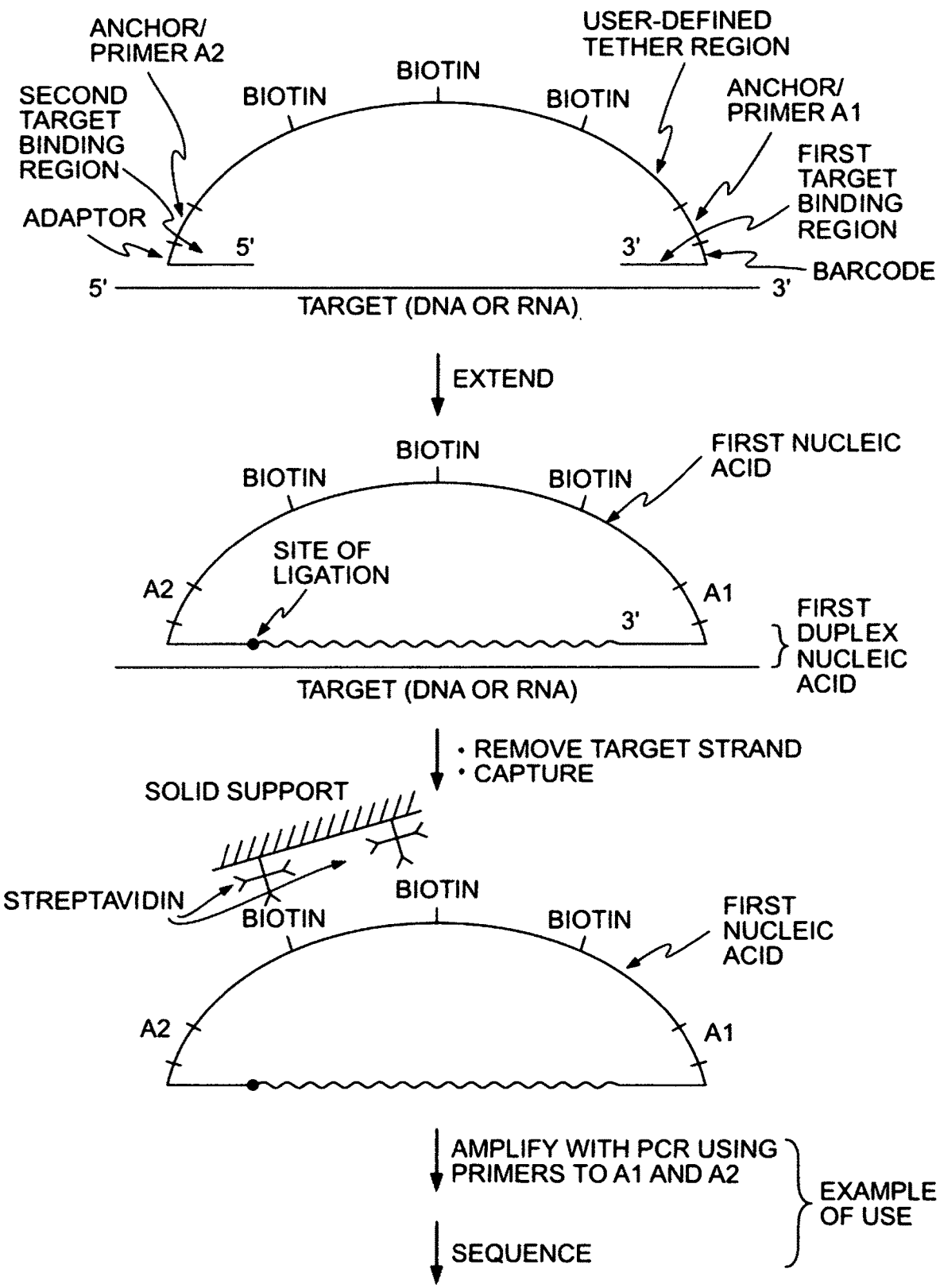

METHODS FOR AMPLIFICATION OF NUCLEIC ACIDS UTILIZING CLAMP OLIGONUCLEOTIDES

CROSS-REFERENCE TO RELATED APPLICATIONS

This application is a divisional patent application of patent application Ser. No. 14/773,365 filed 7 Sep. 2015, which is a non-provisional patent application of provisional patent application Ser. No. 61/789,685 flied Mar. 15, 2013 and claims the benefit of the filing date of PCT/US2014/029850 filed 14 Mar. 2014 under 35 U.S.C. § 371 from which the PCT application claims priority.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION

(1) Field of the Invention

The present invention relates to methods of amplification of nucleic acids. Specifically, nucleic acid amplification using clamp oligonucleotides.

(2) Description of Related Art

There are a variety of methods for the amplification of nucleic acids known to those skilled in the art. Providing a method for the selectively capturing a target nucleic acid present in a sample can be useful for purifying, amplifying and/or detecting that specific target. The present invention provides methods for capturing specific nucleic acid targets for further manipulation, including amplification and sequencing.

BRIEF SUMMARY OF THE INVENTION

The present invention provides methods of immobilizing and amplifying a target nucleic acid. In one method, a clamp oligonucleotide is mixed with a target nucleic acid. The clamp oligonucleotide comprises a first target-binding region on the 3'-terminus and a second target-binding region on the 5'-terminus and user-defined tether region between the first and second target binding regions. The tether region may comprise a variety of user-defined sequences or elements. For example, the tether region may comprise one or more of the following and in any combination, a primer site, an anchor site and/or a barcode. Preferably, the tether region contains at least one capture element and at least one primer-binding site.

The first and second target binding regions of the clamp oligonucleotide are annealed to the target nucleic acid. The clamp oligonucleotide is extended by polymerase from its '3-terminus to its 5'-terminus to produce a first duplex nucleic acid. The first duplex contains a first nucleic acid and the target nucleic acid. The ends of the first nucleic acid are joined by ligase to produce a circularized nucleic acid. The circularized nucleic acid is removed from the target nucleic acid and then captured by a capture means provided on a solid support. Capture may be achieved by a variety of methods known in the art. Preferably the capture means binds the capture element of the tether region. Alternatively, the circularized first nucleic acid/target complex may be captured onto a solid support, then the first nucleic acid separated from the target nucleic acid.

A primer able to bind the at least one primer binding site of the tether region is mixed with the circularized nucleic acid and extended using polymerase to produce a second nucleic acid duplex containing a second nucleic acid and the first nucleic acid. The second nucleic acid, or the amplified target nucleic acid, is removed from the first nucleic acid and may now undergo further manipulation, including amplification using PCR, capture, detection and/or sequencing, including next generation sequencing.

Other aspects of the invention are found throughout the specification.

BRIEF DESCRIPTION OF THE DRAWINGS

FIG. 1 is a schematic diagram of one method of the present invention.

DETAILED DESCRIPTION OF THE INVENTION

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA. In addition, oligonucleotides may be nuclease resistant and include but are not limited to 2'-O-methyl ribonucleotides, phosphorothioate nucleotides, phosphorodithioate nucleotides, phosphoramidate nucleotides, and methylphosphonate nucleotides.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension.

In addition, primers may be nuclease resistant and include primers that have been modified to prevent degradation by exonucleases. In some embodiments, the primers have been modified to protect against 3' or 5' exonuclease activity. Such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill.

The term "support" or "solid support" refers to conventional supports that include, for example, polymers such as microtiter wells, beads, particles or fibers, and silane or silicate supports such as glass slides or tubes to which capture molecules are covalently or non-covalently bound.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, swabs (nasopharyngeal, rectal, ocular, urogenital, etc.), organs, muscle, bone marrow, FFPE tissue, skin, tumors and/or cells obtained from any part of the organism; plant material, cells, fluid, etc.; an individual bacterium, groups of bacteria and cultures thereof; food; cosmetics; drugs/pharmaceuticals; materials prepared via bioprocessing (finished product as well as intermediate materials); water; environmental samples, including but not limited to, for example, soil, water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like.

The term "amplifying" or "amplification" as used herein refers to the process of creating nucleic acid strands that are identical or complementary to a complete target nucleic acid sequence, or a portion thereof, or a universal sequence that serves as a surrogate for the target nucleic acid sequence.

The term "affixed" as used herein refers to the attachment of a molecule(s), such as the first and second oligonucleotides, to a solid support. A wide variety of methods commonly known in the art can be used for attachment. One preferred method is covalent attachment.

The term "nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions.

Nitrogenous bases may be conventional bases (A, G, C, T, U), non-natural nucleotides such as isocytosine and isoguanine, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121).

Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43 (42):13233-41).

The term "releasing" or "released" as used herein refers to separating the desired amplified nucleic acid from its template by heating the duplex to a temperature that denatures the nucleic acid duplex forming two separate oligonucleotide strands.

The term "removing" as used herein refers to a variety of methods used to isolate or otherwise remove and separate one nucleic acid strand of a duplex from another, such as for example enzymatic, thermal and/or chemical digestion, degradation and/or cleavage of one of the strands of the duplex, or denaturation/dissociation of the strands by heat, acoustic energy, chemicals, enzymes or a combination thereof.

The terms "tag region" or "tag sequence" refer to a user-defined nucleic acid sequence or sequences that are incorporated into an oligonucleotide or other nucleic acid structure, such as a primer, to provide one or more desired functionalities. Examples of such elements include, for example, adapters, sequencing primers, amplification primers, capture and/or anchor elements, hybridization sites, promoter elements, restriction endonuclease site, detection elements, mass tags, barcodes, binding elements, and/or non-natural nucleotides. Other elements include those that clearly differentiate and/or identify one or more nucleic acids or nucleic acid fragments in which a tag sequence has been incorporated from other nucleic acids or nucleic acid fragments in a mixture, elements that are unique in a mixture of nucleic acids so as to minimize cross reactivity and the like and elements to aid in the determination of sequence orientation. Some or all of the elements in a tag sequence can be incorporated into amplification products.

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, in some cases referred to as an identical sequence, as well as complementarity sufficient to achieve the desired binding of nucleic acids. Correspondingly, the term "complementary hybrids" encompasses substantially complementary hybrids.

The term "anchor sequence" or "anchor" as used herein refers to a user-defined sequence that is added onto a nucleic acid target sequence, often by incorporation via a tag sequence. The anchor may be used to facilitate subsequent processing, such as sequencing, for example, to purify, capture, immobilize or otherwise isolate the target nucleic acid bearing the anchor.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79 (22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4 (1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proofreading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* (3rd Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include the 7500 Fast Dx real-time instrument (which is also capable of high-resolution melting curve analyses) (Life Technologies, Carlsbad, Calif.) and the 3500xl capillary gel instruments. Other instruments known in the art to be useful in the methods of the present invention are also contemplated for use by one of skill in the art in practicing the methods of the present invention.

The present invention is a method for selectively capturing a target nucleic acid of interest and preparing a target template for further manipulation utilizing a clamp oligonucleotide. For example, a clamp oligonucleotide complexed to the target nucleic acid may be utilized to create a circularized template. This template may then be isolated for further manipulations such as, for example, amplification, detecting, quantitating and sequencing, including next generation sequencing.

In one embodiment, the clamp oligonucleotide comprises two target nucleic acid binding regions, one on each end separated by a tether region. This tether region may include a variety of functional sequences including, for example, one or more primer sites (e.g. primer sites located at opposite ends of the tether region, but inside the target binding regions), one or more anchor sites, one or more adapter sites, one or more detection sites, one or more sequencing primer binding sites and/or one or more barcodes. The tether region also provides the length required to allow binding of the two target binding regions at the desired locations on the target.

In another embodiment the tether region may further comprise other chemical molecules for particularly desired functions. For example, molecules that can be utilized to effect target capture may be situated at one or more locations along the tether region. For example, biotin incorporated at one or more location in the clamp oligonucleotide facilitates immobilization of the clamp oligonucleotide/target nucleic acid complex onto a streptavidin-modified solid support. Similarly, digoxigenin incorporated at one or more location in the clamp oligonucleotide facilitates immobilization of the clamp oligonucleotide/target nucleic acid complex onto anti-digoxigenin antibody-modified solid support. Alternately, a specific, user-defined capture sequence included in the tether region of the clamp oligonucleotide facilitates immobilization of the clamp oligonucleotide/target nucleic acid complex onto solid support to which the complement to the specific capture sequence is bound.

In one aspect, the target binding regions contain sequences complementary to the target nucleic acid of interest, thus facilitating specific binding. In one method of the present invention, the clamp oligonucleotide and a sample containing the target(s) of interest are combined or mixed. In this example, the clamp oligonucleotide is modified to contain biotin along the tether region. The two target binding regions of the clamp oligonucleotide are annealed to the target nucleic acid. These regions are selected to be a desired distance from each other within the target nucleic acid sequence. The clamp oligonucleotide is extended from the 3'- to the 5'-terminus and the ends are joined by ligase to produce a circularized nucleic acid containing the complement of a segment of the target sequence and the clamp oligonucleotide. The circularized nucleic acid is removed from the target nucleic acid and captured from solution using, for example, a streptavidinylated (or other appropriate binding partner) solid support that will tightly bind a biotinylated clamp oligonucleotide.

The captured circularized nucleic acid can now undergo further manipulation. For example, the circularized nucleic acid can be amplified using methods known in the art, including PCR and rolling circle amplification. Primer sites can be chosen within the sequence associated with the original target nucleic acid or within sequence in the user-defined tether region, or a combination of the two. If primers are within the tether region, the same primers can be used for different clamp oligonucleotides generated from multiple target nucleic acids, allowing universal amplification in a multiplex format. Furthermore, adapters, barcodes and sequencing primer sites, for example, may be utilized to easily generate templates for sequencing, including next generation sequencing. Also, the target nucleic acid in the clamp oligonucleotide generated circular template may be sequenced directly. Other functions known to those skilled in the art may be performed as well.

In another aspect of this embodiment, the target binding regions of the clamp oligonucleotide may be random, allowing binding to all sequences within the genome or transcriptome for applications such as whole genome or whole transcriptome amplification. Alternatively, the target binding regions may be semi-random, designed to include some specific sequences of the target nucleic acid, for example, particular regions of the genome, as well as some random regions to allow binding to many different potential sequences within the targeted regions. The target binding regions may also be less random, designed to bind, for example, to particular types of nucleic acids, such as non-ribosomal RNA transcripts.

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

What is claimed is:

1. A non-rolling amplification method for amplifying a target nucleic acid, said method comprising the steps of:
   annealing first and second target binding regions to a target nucleic acid in a first mixture comprising a clamp oligonucleotide and a target nucleic acid, wherein said clamp oligonucleotide comprises said first target binding region on the 3'-terminus and said second target binding region on the 5' terminus and user-defined tether region between said first and said second target binding regions, wherein said tether region comprises one or more capture elements, and extending said clamp oligonucleotide across said target nucleic acid to produce a first duplex containing a first nucleic acid and said target nucleic acid;
   ligating the ends of said first nucleic acid to produce a circularized nucleic acid;
   removing said circularized nucleic acid from said target nucleic acid;
   digesting the uncircularized clamp oligonucleotide enzymatically to remove uncircularized clamp oligonucleotide from circularized nucleic acid; and
   capturing said circular nucleic acid on a solid support wherein said solid support contains a capture means to bind said capture element of said tether region in a second mixture comprising a primer able to bind said at least one primer binding site of said tether region and expanding said primer to produce a second nucleic acid duplex containing a second nucleic acid and said first nucleic acid.

* * * * *